United States Patent [19]

McGill

[11] Patent Number: 4,589,171
[45] Date of Patent: May 20, 1986

[54] DEVICE FOR HOLDING AND POSITIONING TUBING OF I.V. ADMINISTRATION SET

[75] Inventor: Lee E. McGill, Orinda, Calif.

[73] Assignee: Miles Laboratories, Inc., Elkhart, Ind.

[21] Appl. No.: 592,993

[22] Filed: Mar. 23, 1984

[51] Int. Cl.⁴ .......................... A44B 21/00; F16K 7/06
[52] U.S. Cl. ........................................ 24/543; 24/544; 128/346; 251/6; 137/1; 604/30; 604/246
[58] Field of Search ............ 24/543, 544, 688, 30.5 R, 24/30.5 P, 30.5 L, 30.5 S, 704, 297; 128/346; 604/30, 65, 246; 251/6; 137/1

[56] References Cited

U.S. PATENT DOCUMENTS

| D. 234,204 | 1/1975 | Miller et al. | 24/543 |
| 2,818,871 | 1/1958 | Beaudry | 24/30.5 P |
| 3,106,919 | 10/1963 | Churchville | 128/346 |
| 3,316,910 | 5/1967 | Davis | 604/30 |
| 3,685,787 | 8/1972 | Adelberg | 251/6 |
| 3,854,482 | 12/1974 | Laugherty et al. | 24/543 |
| 3,893,468 | 7/1975 | McPhee | 251/6 |
| 4,053,135 | 10/1977 | Saliaris | 24/543 |
| 4,193,174 | 3/1980 | Stephens | 128/346 |
| 4,378,617 | 4/1983 | Burns | 24/543 |
| 4,382,453 | 5/1983 | Bujan et al. | 24/543 |
| 4,453,295 | 6/1984 | Laszczower | 24/543 |
| 4,470,173 | 9/1984 | Adamson | 24/30.5 P |

Primary Examiner—Victor N. Sakran
Attorney, Agent, or Firm—James A. Giblin

[57] ABSTRACT

Device for holding and positioning plastic tubing of an intravenous fluid administration set. Device comprises a generally flat, foldable, elongate structure having two outwardly extending arms connected via an intermediate flexible portion having on opposite sides thereof substantially parallel longitudinal recesses which, when the arms are folded against one another, form a longitudinal channel, generally circular in cross section and capable of holding plastic tubing via friction fit. In preferred embodiments, device includes means for irreversibly locking the arms together in a spring-like manner and a tamper prevention and indication means.

5 Claims, 11 Drawing Figures

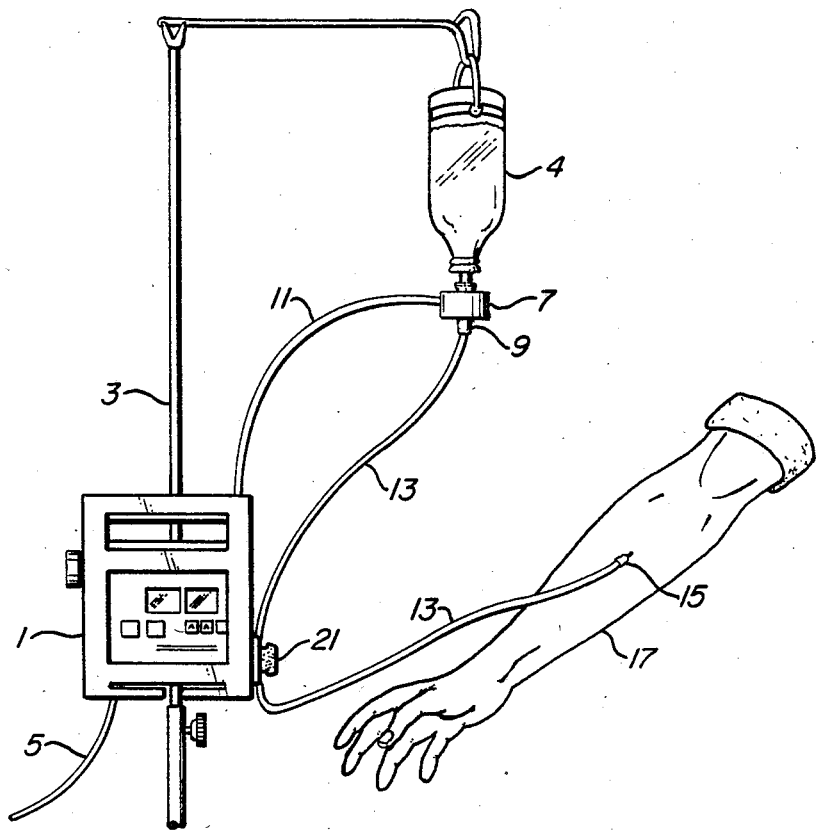
FIG._1.
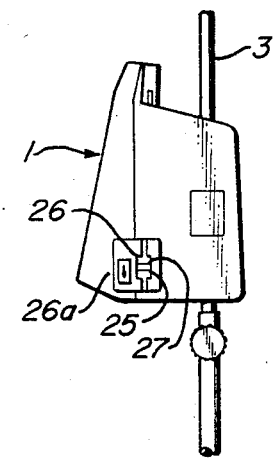
FIG._2.
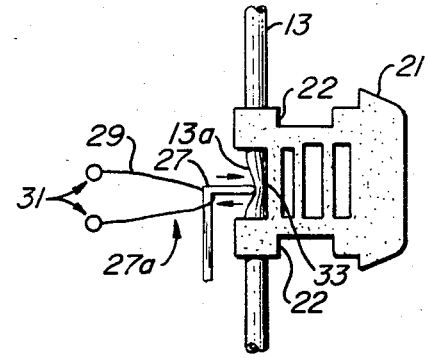
FIG._3.

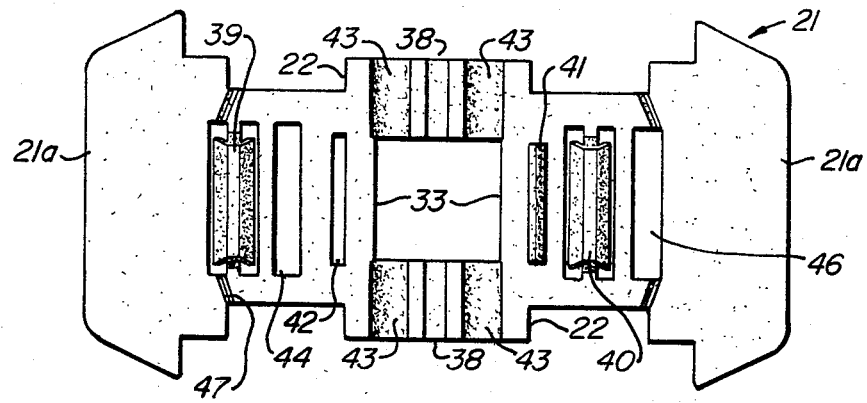
FIG._4.
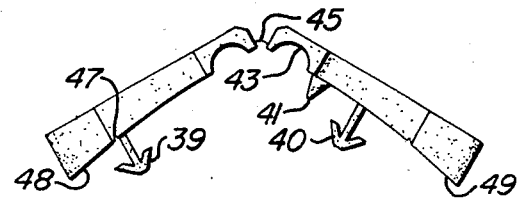
FIG._5.
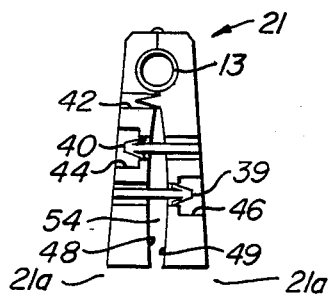
FIG._6.
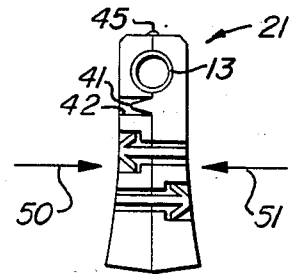
FIG._7.
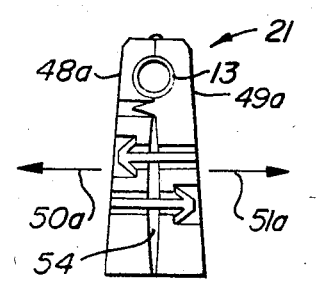
FIG._8.
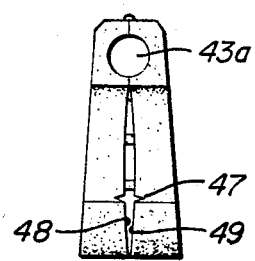
FIG._9.
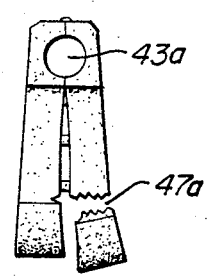
FIG._10.

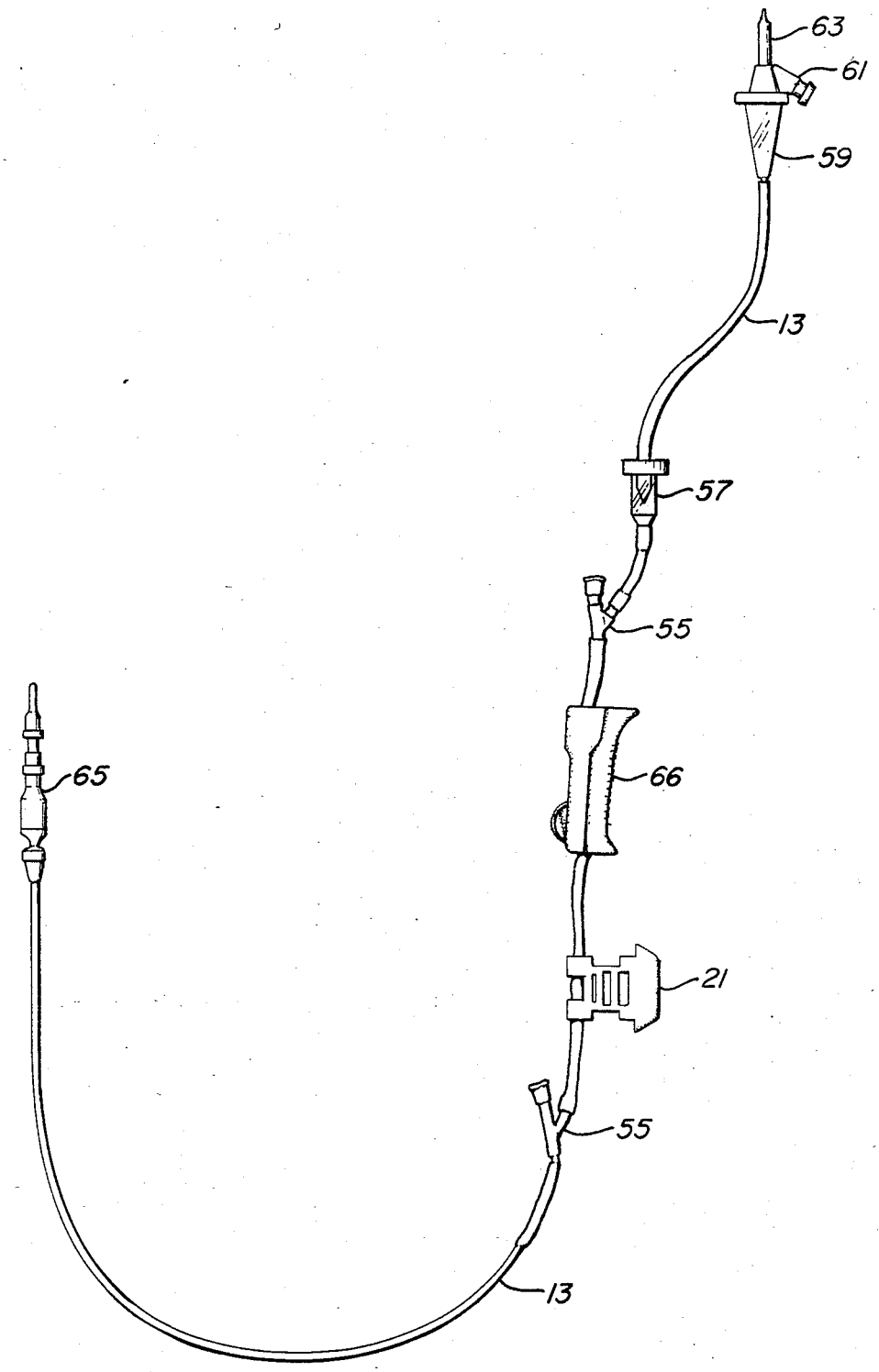
FIG._11.

DEVICE FOR HOLDING AND POSITIONING TUBING OF I.V. ADMINISTRATION SET

BACKGROUND OF THE INVENTION

1. Field:

This disclosure is generally concerned with devices used with intravenous fluid administration sets and specifically with a device adapted for the holding, positioning and insertion of the plastic tubing of such sets into other devices adapted to control fluid flow through such tubing.

2. Prior Art:

Administration sets for intravenous (I.V.) fluids such as dextrose, saline, amino acids, and electrolyte solutions and lipid emulsions are well known and available in a variety of forms. In general, the sets consist of a tubing made from a medically safe plastic material such as polyvinyl chloride having a "spike" end for insertion through the stopper of an I.V. fluid container and an end terminating in a needle (cannula) for insertion into a blood vessel of a patient. The flow of I.V. fluid is controlled by a variety of devices which may be positioned between the ends of the tubing. In the simplest case, the flow is controlled by an external clamp such as the roller clamps of U.S. Pat. No. 3,685,787 to Adelberg or U.S. Pat. No. 3,893,468 to McPhee. In other cases, flow is controlled by various volume control devices which may be an integral part of the I.V. tubing.

In many cases, the control of both the flow rate and flow volume of an I.V. fluid is critical to the safe care of a patient, especially when certain potent drugs are administered with the I.V. fluid. In these cases, it is becoming more common to use various electronic devices designed to provide very high precision in controlling I.V. fluid flow rate or volume. In use, these devices are designed to receive a portion of the plastic tubing of an I.V. administration set. By exerting variable pressure on the tubing in conjunction with a fluid flow or fluid volume monitoring means, such devices are able to provide more accurate control than simpler devices such as simple roller clamps. In addition, such electronic devices are able to provide additional monitoring devices which provide audible and visual signals or automatic shut off if fluid flow falls outside pre-determined conditions. Because of the above features, such electronic devices are being used on a regular basis. In using such devices, however, there must be means for securing at least a portion of the plastic tubing in the monitoring or control device. Ideally, the tubing securing device is one which does enter the tubing and acts externally about the tubing. In addition, the device should be easy to apply and, in certain preferred applications, tamper proof (i.e. once attached it should be unremovable form the tubing without difficulty or detection).

I have devised such a device and it is especially useful in conjunction with a new, relatively low cost I.V. fluid control device described in more detail in U.S. Patent Application Ser. No. 445,390 filed Nov. 30, 1982 in the name of J. Krumme et al and entitled, "Controlled Flow Rate Intravenous Apparatus Employing Shaped Memory Flow Control Element". Details of the device are described below.

SUMMARY OF THE INVENTION

My device for holding and positioning plastic tubing of an I.V. fluid adminsitration set comprises a generally flat, elongate, and foldable polymeric material having a central flexible portion of reduced thickness and two outwardly extending arms. The flexible portion is adapted to serve as a hinge between the foldable arms. On opposite sides of the flexible portion (in its unfolded position) are generally parallel longitudinal grooves or recesses which, when the arms are folded against one another in a folded or closed position, form a longitudinal channel, generally circular in cross section and capable of holding plastic tubing via a friction fit. In an especially preferred embodiment, the longitudinal channel is not continuous but includes an open section which exposes the held tubing to any means capable of controlling fluid flow via application of variable mechanical forces against the exposed portion of the tubing. In other preferred embodiments, the arms include means for irreversibly locking the arms in a closed position and tamper prevention and indication means. In yet other embodiments, the device includes means for guiding the locking means (e.g. barb-like projections on an arm, as described below) into openings in an opposite arm. In yet another embodiment, means for holding the arms in a locked spring-loaded position are provided.

BRIEF DESCRIPTION OF THE FIGURES

FIG. 1 illustrates the overall I.V. administration system in which the device of this disclosure may be used.

FIG. 2 shows a side view of the electronic fluid control device into which the device of this disclosure may be inserted.

FIG. 3 shows detail of one type of electronic fluid control mechanism vis-a-vis the device of this disclosure.

FIG. 4 shows a planar view of the device in its open (unused) position.

FIG. 5 shows a side view of the device in a partially closed position.

FIGS. 6, 7 and 8 shows the function of a preferred locking means for irreversibly locking the device around plastic tubing of an I.V. fluid administration set.

FIGS. 9 and 10 illustrate a preferred tamper-prevention-indication feature.

FIG. 11 illustrates the device as part of a typical I.V. fluid administration set.

SPECIFIC EMBODIMENTS

The device of this disclosure may be made of any material capable of being formed into the configuration described herein and capable of some flexibility when in a thin form at its central portion. Examples of such materials in a polymeric (plastic) form are polypropylene, polyethylene, and ABS (acrylonitrile-butadiene-styrene). In the Example below, I used a glass-filled polypropylene plastic material.

My device can be understood better by reference to the Figures.

FIG. 1 illustrates the overall set up in which the device is used. In FIG. 1, an electronic flow rate controller 1 having an electrical cord 5 is attached to a conventional I.V. stand 3 from which an I.V. fluid container 4 is suspended. Associated with the container is a drop counter 7 in electrical communication via connector 11 to the electronic controller device 1. Continuous with the drop counter 7 at connector spike 9 is a plastic (e.g. PVC) I.V. administration tube 13 held in place in electronic device 1 by the tubing positioner and holder 21 of the present invention. After passing by control device 1 the tubing 13 is insertable via cannula 15 into, for example, the vein of an arm 17.

FIG. 2 shows a side view of control device 1 showing an opening 25 into which tubing holder 21 is inserted. The holder 21 may be retained, for example, by spring loaded retention means at 26 which reversibly catch shoulders 22 (of FIG. 3) and releasable by downward movement of an ejection button 26a which releases the retentin means 26.

FIG. 3 illustrates very generally one method by which fluid control can be achieved. In FIG. 3, tubing holder 21, (shown in closed position about tubing 13) is held in place in controller 1 opening 25 via retention means 26 (not shown). At position 13a, tubing 13 is exposed to a moveable mechanical knife-edge arm 27 which simply presses against the exposed tubing at 13a in conjunction with an arm control means 27a which acts electrically in conjunction with (for example) drop counter 7 to regulate fluid flow by increasing or decreasing pressure at area 13a by pressing tubing 13 via arm 27 against a flat backing 33. In one preferred embodiment I used a nitinol wire controlled device of the type described in U.S. Patent Application Ser. No. 445,390, described above. This is generally shown as nitinol wire 29 in electrical contact with electrical posts 31. As described in that application, precise control of fluid flow is obtained by increasing or decreasing the amount of current flowing through (and heat in) wire 29 in response to signals from drop controller 7 (for example).

FIGS. 4 and 5 show one embodiment of the holding device of this disclosure in an open, flat and a partially closed form. In a preferred embodiment, the device 21 (about 2½×1×⅛ inches) includes approximately ⅛" barb-like projections 39 and 40 (seen better in FIG. 5) which look into corresponding slots 46 and 44 on opposite arms when the arms are folded together. A longitudinal alignment bar 41 folds into alignment slot 42. At the middle of device 21 is an opening 33 which, when the device is folded, correspond to the tubing exposure opening 13a in FIG. 3. Thinned flexible sections 38 (less than 1/16" thick) open hinges for the two outwardly extending arms 21a of device 21. On adjacent sides of flexible sections 38 (of reduced thickness) are recesses 43 which, when the arms are folded together, form longitudinal channels, generally circular in cross section and shown as 43a in FIGS. 9 and 10. Channels 43a have dimensions sufficient to hold tubing 13 in a relatively tight, but non-fluid flow-reducing, friction fit.

In FIG. 5 the device 21 is shown in a side view, partially closed position to illustrate the barbed locking means 39 and 40 and aligment means 41. In preferred embodiments the arms 21a of device 21 include notches 47 (see FIGS. 9 and 10) designed to break arms 21a if the arms 21a are pulled apart after the barbed projections 39 and 40 are locked into slots 46 and 44.

FIGS. 6, 7 and 8 illustrate in cross sectional views the locking means in more detail. In FIG. 6, the device has been folded about tubing 13 but the tops of the barbed projections 39 and 40 have not yet been pushed fully through slots 46 and 44 respectively. The width of the "wings" of the barbs of 39 and 40 are slightly larger than slots 46 and 44. The thicknesses at the distal ends of arms 21a, as shown at 48 and 49, is slightly greater than at proximal ends 48a and 49a (of FIG. 8). Because of this, and as shown in FIG. 7, ends 48 and 49 interfere, leaving a gap 54, and it is necessary to exert forces (shown by arrows 50 and 51) at about the middle of each arm 21a to force the slightly wider heads (or wings) or barbed projections 39 and 40 through slots 46 and 44, compressing the winged barbed heads of the projections 39 and 40.

After the winged heads have fully entered slots 46 and 44, they expand or spring out to irreversibly lock the device 21 in a folded, closed position about tubing 13. After compressive forces 50 and 51 are released and the barbs 39 and 40 fully engaged in slots 46 and 44, the added thicknesses 48 and 49 (of FIG. 6), in conjunction with closed flexible hinge portion 45 and thinner portions of proximal arms 48a and 49a (FIG. 8), tend to create opposite forces shown by arrows 50a and 51a in FIG. 8, tending to push middle portions of arms apart (see gap 54) even though the device 21 itself is in a locked, folded position about tubing 13.

FIGS. 9 and 10 show a side view of the folded device 21 and illustrate generally the longitudinal, transverse notches 47 which serve as a means of discouraging (or at least indicating) tampering with the device 21 when locked. If an attempt is made to pull the distal arms of the device 21 apart after it is locked in a folded position, at least one of the notches 47 will break, as shown via broken arm 47a. Since these notches are located distal to the locking barb-like projections 39 and 40, breakage of the arm will not unlock the device.

FIG. 11 illustrates the device 21 as part of a typical I.V. fluid administration set comprising a cannula end 65, tubing 13, an injection "Y" 55, the device 21, a roller clamp 66, another injection "Y" 55, a check valve 57, a drip chamber 59, an air vent 61 and a stopper spike 63.

As used herein, the expression friction fit, in reference to I.V. set tubing, refers to the use of a clamping force sufficient to hold the tubing with a snug fit within the device disclosed herein but without interfering with fluid flow through the tubing. In other words, the fit of the tubing within tubing retention channel must be tight enough to firmly grasp the tubing but not so tight as to significantly compress the tubing or interfere with fluid flow. Such friction fit can be obtained by assuring that the longitudinal channel of the device (e.g. 43a of FIGS. 9 and 10) is slightly smaller in cross section than the outer diameter of the tubing.

It should be understood that the above Example is merely illustrative and that, given this disclosure, variations will occur to those skilled in the art. Accordingly, it is intended that the scope of this invention should be limited only by the following claims.

I claim:

1. A device for holding and positioning plastic tubing of an intravenous fluid administration set, the device comprising a generally flat, elongate and foldable polymer structure having two outwardly extending arms connected via an intermediate flexible portion adapted to serve as a hinge for the two arms, the flexible portion having on opposite sides thereof substantially parallel longitudinal recesses which, when the arms are folded against one another, form a longitudinal channel, generally circular in cross section and capable of holding plastic tubing via a relatively tight, but non-fluid-flow-reducing friction fit, the arms including means for irreversibly locking the arms in a closed position.

2. The device of claim 1 wherein at least one arm includes a projection adapted to be inserted into a slot in the opposite arm when the arms are folded together, the projection and opening in the opposite arm being located between the flexible portion and the locking means.

3. The device of claim 1 wherein at least one arm has a distal end and a proximal end adjacent the flexible portion, the thickness near the distal end being greater than the thickness at the proximal end, the thickness difference adapted to provide a compressed spring-like force between the arms and tending to push the arms apart when they are folded against each other in a locked position.

4. The device of claim 1 wherein at least one arm includes a scored portion of reduced thickness adapted to provide means for breaking that arm if an attempt is made to defeat the locking means by pulling the arms apart after they have been folded against one another in a locking relationship.

5. A device for holding and positioning plastic tubing of an intravenous fluid administration set, the device comprising a generally flat, elongate and foldable structure having two outwardly extending arms connected via an intermediate flexible portion of reduced thickness, the flexible portion adapted to serve as a hinge for the two arms, the flexible portion having on adjacent sides thereof substantially parallel longitudinal recesses which, when the arms are folded against one another, form at least one longitudinal channel, generally circular in cross section and capable of holding plastic tubing in a relatively tight, but non-fluid-flow-reducing friction fit; the arms each including barb-like projections adapted to be irreversibly inserted into openings in the opposite arm when the arms are folded together; the arms comprising proximal ends connected to the flexible portion and outwardly extending distal ends, the thickness of the distal ends being greater than the thickness of the proximal ends.

* * * * *